(12) United States Patent
LaPorte et al.

(10) Patent No.: US 10,384,032 B2
(45) Date of Patent: Aug. 20, 2019

(54) SYSTEMS AND METHODS FOR MANAGING AMBIENT CONDITIONS

(71) Applicant: Luma LLC, Provo, UT (US)

(72) Inventors: Wesley David LaPorte, Provo, UT (US); Daniel Harrison Barnes, Orem, UT (US)

(73) Assignee: Luma LLC, Lindon, UT (US)

( * ) Notice: Subject to any disclaimer, the term of this patent is extended or adjusted under 35 U.S.C. 154(b) by 83 days.

(21) Appl. No.: 15/390,174

(22) Filed: Dec. 23, 2016

(65) Prior Publication Data

US 2018/0177974 A1  Jun. 28, 2018

(51) Int. Cl.
*A61M 21/02* (2006.01)
*A61M 21/00* (2006.01)
*A61B 5/00* (2006.01)

(52) U.S. Cl.
CPC .......... *A61M 21/02* (2013.01); *A61B 5/4836* (2013.01); *A61B 5/4809* (2013.01); *A61B 5/4812* (2013.01); *A61B 2562/0223* (2013.01); *A61M 2021/0016* (2013.01); *A61M 2021/0027* (2013.01); *A61M 2021/0044* (2013.01); *A61M 2021/0083* (2013.01); *A61M 2205/3375* (2013.01); *A61M 2205/502* (2013.01)

(58) Field of Classification Search
CPC .................. A61M 21/00; A61M 21/02; A61M 2021/0016; A61M 2021/0027; A61M 2021/0044; A61M 2021/0083; A61B 5/4809; A61B 5/4812
See application file for complete search history.

(56) References Cited

U.S. PATENT DOCUMENTS

2007/0083079 A1* 4/2007 Lee ................... A61B 5/4806
                                                        600/27
2011/0160619 A1* 6/2011 Gabara ................. A61B 5/16
                                                        600/595
2017/0319816 A1* 11/2017 Sokol ................... A61M 21/02

* cited by examiner

*Primary Examiner* — Carrie R Dorna
(74) *Attorney, Agent, or Firm* — Stoel Rives LLP

(57) ABSTRACT

A system for generating ambient conditions to improve sleep comprises an ambient condition controller. The ambient condition controller may control a light, a speaker, and multiple diffusers. The system may include a computer-readable non-transitory storage medium having instructions that, when executed by a processor, cause the processor to implement a sleep program. The sleep program may cause the ambient condition controller to be configured in a variety of states over a period of time.

20 Claims, 10 Drawing Sheets

SYSTEMS AND METHODS FOR MANAGING AMBIENT CONDITIONS

TECHNICAL FIELD

The disclosure relates to systems for generating ambient conditions, and more specifically, to generating ambient conditions to improve sleep.

BRIEF DESCRIPTION OF THE DRAWINGS

This disclosure includes and references the accompanying drawings, which provide a more particular description of the embodiments disclosed herein. The disclosure, however, is not limited to the particular embodiments depicted in the figures. The teachings of the disclosure may be utilized and/or adapted to other embodiments, and/or changes may be made to the disclosed embodiments, without departing from the scope of the disclosure.

DETAILED DESCRIPTION

Figure 1A:
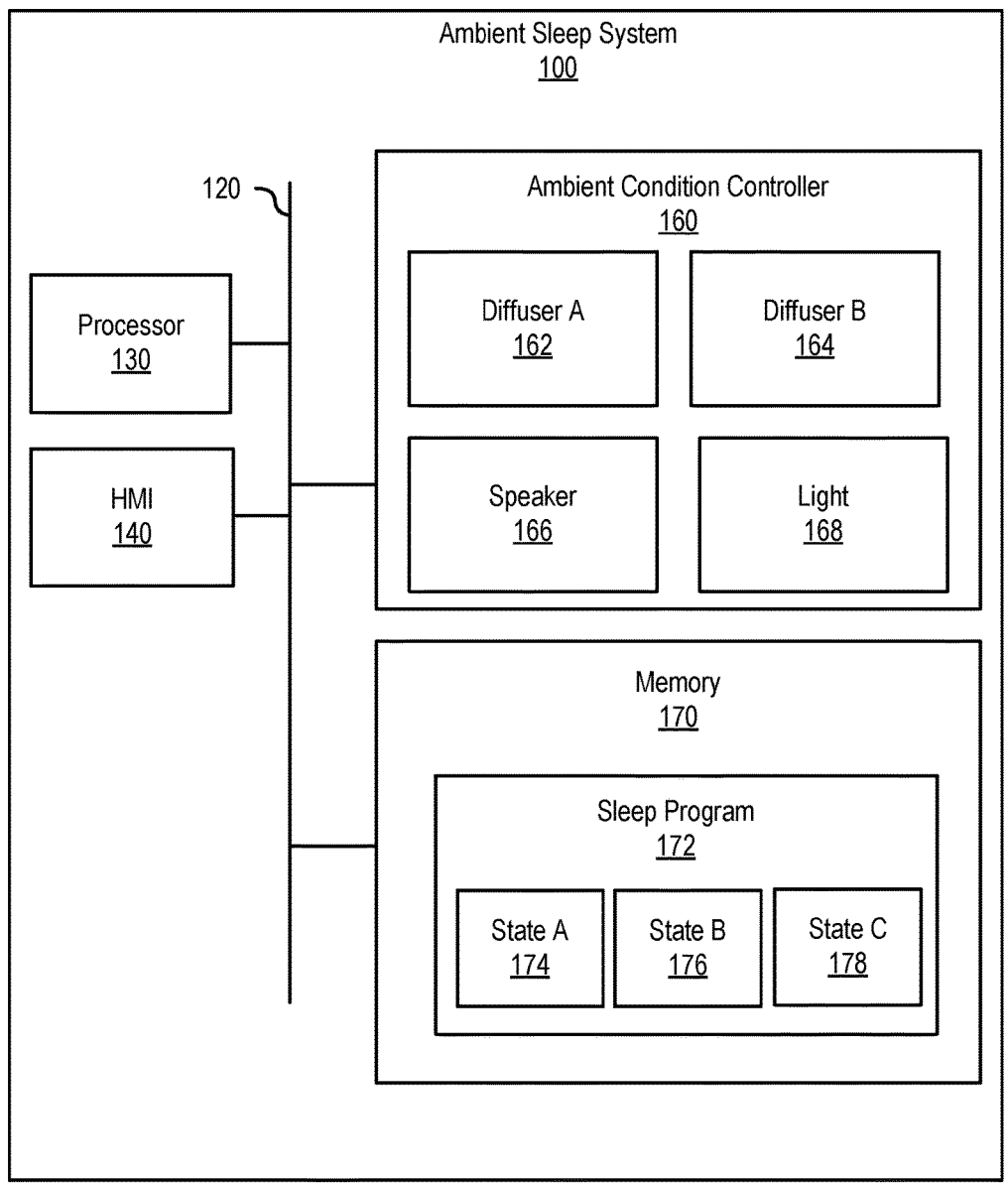
FIG. 1A is a block diagram of one embodiment of an ambient sleep system.

Sleep is one of the basic fundamental needs of humans. Unfortunately, sleep is often interrupted because of an uncontrolled sleeping environment resulting in sudden noises, unanticipated light, unsatisfactory temperature and the like. Disclosed herein are embodiments of apparatus, systems, and methods for automatically generating ambient conditions to improve sleep (ambient sleep systems and methods). Ambient sleep systems may include a processor, an ambient condition controller, and a storage medium containing a sleep program with operating instruction to configure the ambient condition controller.

In one embodiment, the ambient condition controller may include at least two diffusers. Each diffuser may be capable of dispersing a different scent. Further, the sleep program may contain instructions to configure the ambient condition controller to enter a first state while the user is falling asleep, a second state while the user is asleep, and a third state while the user is waking up.

In the first state corresponding to the user falling to sleep, the ambient condition controller may disperse a first scent. The first scent may be diffused from an essential oil intended to assist the user in relaxing, including but not limited to: lavender, jasmine, rose, sandalwood, or the like. The ambient condition controller may remain in the first state for a length of time as specified by the sleep program (first cycle interval). During the first cycle interval, the intensity of the first scent may be varied. For example, the first scent may begin the first cycle interval with a first intensity then logarithmically decrease the intensity as the first cycle interval progresses.

In the second state corresponding to the user being asleep, the ambient condition controller may disperse a second scent. The second scent may be diffused from an essential oil intended to assist the user with sleeping. For example, the second scent may be the same scent as the first scent, a different quantity of the same scent, or a similar scent. The ambient condition controller may remain in the second state for a length of time as specified by the sleep program (second cycle interval). During the second cycle interval, the intensity of the second scent may be varied. For example, the ambient sleep system may detect a user waking up prior to a desired time. In response, the ambient condition controller may increase the intensity of the second scent. Alternatively, the second scent may only be dispersed if the ambient sleep system may detect a user waking up prior to a desired time.

In the third state corresponding to the user being asleep, the ambient condition controller may disperse a third scent. The third scent may be diffused from an essential oil intended to assist the user with waking up, including but not limited to: citrus, peppermint, rosemary, eucalyptus, or the like. The ambient condition controller may remain in the third state for a length of time as specified by the sleep program (third cycle interval). During the third cycle interval, the intensity of the third scent may be varied. For example, the third scent may begin the first cycle interval with a first intensity then exponentially increase the intensity as the first cycle interval progresses.

In some embodiments, the ambient sleep system may include a receiver to receive sleep monitoring data from a sleep monitoring device. The sleep monitoring device may be associated with the ambient sleep system or a separate third-party device, such as a smartwatch, a fitness tracker, a cellular phone, sensor pad, or the like. The ambient sleep system may determine a sleep state of a user based on the received sleep monitoring data. The sleep program may contain instructions that configure the ambient condition controller based on the sleep state. For example, the ambient condition controller may enter a first state in response to determining the user is awake and attempting to fall to sleep, a second state in response to determining the user is awakening prior to a target time period, and a third state in response to determining the user is awakening within a target time period. Further, the ambient condition controller may enter another embodiment in response to determining the user is asleep. The state may be altered based on the sleep stage. For example, the ambient condition controller may enter a certain state in response to determining the user is in a rapid eye movement stage of sleep, and a different state in response to determining the user is in a non-rapid eye movement stage of sleep. Each of these states may define a unique ambient condition.

The ambient conditions may be generated by devices in communication with the ambient condition controller. The ambient condition controller may be configured to send and receive signals to a plurality of devices to monitor and adjust ambient conditions. In some embodiments, the devices may be local to the ambient condition controller. In other embodiments, the ambient condition controller may communicate with a set of peripheral devices that are remote from the ambient controller. In yet other embodiments, the ambient condition controller may use a combination of local devices and remote peripheral devices to generate ambient conditions.

In some embodiments, the devices may include speakers, diffusers, and an illumination device. The illumination device may be capable of producing different hues and adjusting the brightness level. The hue and the brightness level of the illumination device may be altered based on the state of the ambient condition controller. For example, when the ambient condition controller is in a state corresponding to falling to sleep, the light brightness level may become dimmer over time. Whereas, when the ambient condition controller is in a state corresponding to waking up, the light brightness may gradually adapt the brightness and/or hue to simulate a sunrise. Similarly the audio from the speakers and scent from the diffusers may vary based on the state of the ambient condition controller. By using speakers, diffusers, and an illumination device, the ambient condition controller may control, or at least mask, the surroundings of a user. The devices may be integrated in one structure such as a lamp.

In other embodiments, peripheral devices may be physically separated throughout a room or a house, but communicatively coupled to the ambient condition controller. For example, the ambient condition controller may communicate with personal electronic devices (PEDs), appliances, and household systems such as the HVAC system, fans, lights, home theater systems and the like. These peripheral devices may allow the ambient condition controller to create more immersive surroundings. For instance, by communicating with the HVAC system, the ambient condition controller may lower the temperature when a user is asleep.

In some embodiments, the sleep program may be user defined and/or configurable. For example, the user may select the scent, lighting conditions, and sound for each of the states of the ambient condition controller. The duration the ambient condition controller remains in each of the states may also be configurable. For example, a user may program the duration of each state prior to the sleep program begins. Alternatively or additionally, the ambient sleep system may include an interface to receive a user input indicating that the user falling asleep faster or slower than normal. The ambient sleep system may adjust the duration of a state based on the user input. For example, in response to the user input, the ambient sleep system may enter another state, reduce the remaining duration of the current state, or extend the remaining duration of the current state.

The sleep program may be time based, duration based, or sleep cycle based. For example, the ambient condition controller may be automatically configured to enter certain states based on the time of day. Alternatively, a user may supply a desired sleep duration and the sleep program may adapt based on the desired sleep duration. For example, a user may specify the amount of hours he/she desires to sleep, or the number of sleep cycles.

In some embodiments, the sleep program may be adaptable based on sleep monitoring data from a sleep monitoring device. For example, the length of time that the ambient condition controller remains in each state may be determined based on sleep monitoring data. For instance, the ambient condition controller may remain in a state corresponding to a user falling to sleep until the sleep monitoring data indicates that the user is asleep.

In some embodiments, the user may specify a target wake time and a wake window. The target wake time may be the time the user desires to wake up. The wake window may be a period of time the user is willing to wake up during. For example, the user may set the target wake time to 7:00 AM and the wake window between 6:30 AM-7:00 AM. If the sleep monitoring data indicates that the user is waking up during the wake window, the ambient condition controller may enter a state associated with waking up. The duration and the intensity of the ambient condition may be adapted based on the time until the target wake time. For instance, the ambient condition controller may extend the state associated with waking up so that the user wakes up as close to the target wake time as possible while ensuring the user does not fall back into a deeper sleep cycle.

In some embodiments, the ambient sleep monitor may be configured to communicate with a PED. For example, a user may use a smart phone application to configure the sleep program and/or the current state of the ambient condition controller. The smart phone application may also be used to access sleep monitoring data, such as sleep metrics. Further, the ambient sleep system may adjust the PED as part of an ambient condition state. For example, the ambient sleep system may request to change settings of the PED when the ambient condition controller enters each state. For instance, when the ambient condition controller enters a state associated with falling to sleep, the PED screen may be dimmed and the notifications silenced.

Additional details and examples are provided with reference to the figures below. Generally speaking, the systems and methods disclosed herein may be adapted to interface with or be included as part of any environmental control systems, such as smart home systems, lighting systems, alarm systems, and the like.

Embodiments may include various steps, which may be embodied in machine-executable instructions to be executed by a computer system. A computer system may include one or more general-purpose or special-purpose computers (or other electronic devices). The computer system may include hardware components that include specific logic for performing the steps or may include a combination of hardware, software, and/or firmware.

Some of the infrastructure that can be used with embodiments disclosed herein is already available, such as: general-purpose computers, computer programming tools and techniques, digital storage media, and communications networks. A computer may include a processor, such as a microprocessor, microcontroller, logic circuitry, or the like. The processor may include a special-purpose processing device, such as an ASIC, PAL, PLA, PLD, CPLD, Field Programmable Gate Array (FPGA), or other customized or programmable device. The computer may also include a computer-readable storage device, such as non-volatile memory, static RAM, dynamic RAM, ROM, CD-ROM, disk, tape, magnetic, optical, flash memory, or other computer-readable storage medium.

Suitable networks for configuration and/or use, as described herein, include any of a wide variety of network infrastructures. Specifically, a network may incorporate landlines, wireless communication, optical connections, various modulators, demodulators, small form-factor pluggable (SFP) transceivers, routers, hubs, switches, and/or other networking equipment.

The network may include communications or networking software, such as software available from NOVELL®, MICROSOFT®, ARTISOFT™, and other vendors, and may operate using TCP/IP, SPX, IPX, SONET, and other protocols over twisted pair, coaxial, or optical fiber cables, telephone lines, satellites, microwave relays, modulated AC power lines, physical media transfer, wireless radio links, and/or other data transmission "wires." The network may encompass smaller networks and/or be connectable to other networks through a gateway or similar mechanism.

Aspects of certain embodiments described herein may be implemented as software modules or components. As used herein, a software module or component may include any type of computer instruction or computer-executable code located within or on a computer-readable storage medium, such as a non-transitory computer-readable medium. A software module may, for instance, comprise one or more physical or logical blocks of computer instructions, which may be organized as a routine, program, object, component, data structure, etc., that perform one or more tasks or implement particular data types, algorithms, and/or methods. Various modules may be implemented in hardware, software, firmware, and/or a combination thereof.

A particular software module may comprise disparate instructions stored in different locations of a computer-readable storage medium, which together implement the described functionality of the module. Indeed, a module may comprise a single instruction or many instructions, and may be distributed over several different code segments, among different programs, and across several computer-readable storage media. Some embodiments may be practiced in a distributed computing environment where tasks are performed by a remote processing device linked through a communications network. In a distributed computing environment, software modules may be located in local and/or remote computer-readable storage media. In addition, data being tied or rendered together in a database record may be resident in the same computer-readable storage medium, or across several computer-readable storage media, and may be linked together in fields of a record in a database across a network.

The embodiments of the disclosure can be understood by reference to the drawings, wherein like parts are designated by like numerals throughout. The components of the disclosed embodiments, as generally described and illustrated in the figures herein, could be arranged and designed in a wide variety of different configurations. Thus, the following detailed description of the embodiments of the systems and methods of the disclosure is not intended to limit the scope of the disclosure, as claimed, but is merely representative of possible embodiments.

FIG. 1A is a block diagram of one embodiment of an ambient sleep system 100. The ambient sleep system 100 may comprise a processor 130, a human-machine interface (HMI) 140, an ambient condition controller 160, and memory 170. A bus 120 may interconnect various integrated and/or discrete components. These components may allow the ambient sleep system to generate ambient conditions according to a sleep program 172.

The processor 130 may include one or more general purpose devices, such as an INTEL®, AMD®, or other standard microprocessor. The processor 130 may include a special purpose processing device, such as ASIC, SoC, SiP, FPGA, PAL, PLA, FPLA, PLD, or other customized or programmable device. The processor 130 may perform distributed (e.g., parallel) processing to execute or otherwise implement functionalities of the presently disclosed embodiments.

The memory 170 may include static RAM, dynamic RAM, flash memory, one or more flip-flops, ROM, CD-ROM, DVD, disk, tape, or magnetic, optical, or other computer storage medium. The memory 170 may include one or more sleep programs 172. The memory 170 may be local to ambient sleep system 100, as shown, or may be distributed and/or remote relative to ambient sleep system 100.

The memory 170 may store one or more sleep programs such as sleep program 172. The one or more sleep programs may be pre-programmed or may be created by a user. The sleep programs are adjustable based on a user input. The one or more sleep programs may define an ambient condition schedule. The ambient condition schedule may be a timeline that indicates various changes in scents, sounds, and lighting. The sleep program 172 may include instructions defining a series of states (i.e., state A 174, state B 176, state C 178). The states may include operating parameters/configurations for remote and local devices such as the ambient condition controller 160.

The ambient condition controller 160 may include at least two diffusers (i.e., diffuser A 162, and Diffuser B 164), a speaker 166, and a light 168. As shown, in some embodiments, the diffusers 162 and 164, speaker 166, and the light 168 may be local to the ambient condition controller 160. In alternative embodiments, the ambient condition controller 160 may control a plurality of remote diffusers, a remote speaker, and/or a remote light. The diffusers 162, 164 may each disperse a unique scent. The ambient condition controller 160 may configure the diffusers 162, 164, the speaker 166, and the light 168 (local devices) to produce a variety of ambient conditions.

When the processor 130 executes the sleep program 172 stored in memory 170, the ambient condition controller 160 may configure the local devices according to state A 174, state B 176, state C 178 as scheduled by the sleep program 172. For example, state A 174 may correspond to the user falling to sleep. The operating parameters may instruct diffuser A 162 to disperse its scent, speaker 166 to produce sounds of ocean waves, and light 168 to change hues to replicate a sunset. Further, the operating parameters may instruct diffuser A 162 to gradually reduce the intensity of the scent, speaker 166 to gradually reduce the volume of the sounds, and the light 168 to gradually reduce the brightness level.

The HMI 140 may facilitate interfacing with the ambient sleep system 100. The HMI 140 may comprise one or more input/output components, such as buttons, switches, displays, and the like. The HMI 150 may comprise a status indicator configured to display and/or communicate status information pertaining to the ambient sleep system 100, such as current sleep program, time remaining in the sleep program, current state of the ambient condition controller, scent name, and so on. In some embodiments, the status indicator may comprise one or more visual indicators, such as a Liquid Crystal Display (LCD), one or more light emitting diodes, or the like. The HMI 150 may further comprise an input component configured to receive user input and/or configuration information, such as sleep program parameters, desired sleep time and/or ambient condition controller state adjustments. For example, the an input may enable a user to indicate that he is falling asleep faster/slower than normal, which may cause the ambient sleep system 100 to adjust the cycle accordingly (e.g., cut the sleep cycle off early, or extend the cycle).

In some embodiments, the HMI 150 may include a microphone. The microphone may receive voice commands. In some embodiments, the ambient sleep system 100 may interface with a voice assistant. The ambient sleep system 100 may include the voice assistant, or may use the voice assistant of a connected PED. The voice commands may control the ambient conditions. For example, a user may use voice commands to dim the lighting, increase the volume, or alter the scent. Voice commands may also cause the ambient sleep system 100 to enter the sleep program 172.

In some embodiments, the ambient sleep system 100 may also use the microphone to monitor a user and automatically adjust ambient conditions. For example, the microphone may pick up noises consistent with interrupted sleep, and the ambient sleep system 100 may alter conditions to encourage a user to enter a deeper sleep state. The ambient sleep system 100 may detect specific noise characteristics to determine the current state of a user. For instance, the sound of adjusting sleep positions may have different noise characteristics than a user getting out of bed. The ambient sleep system 100 may be preprogrammed to identify states of a user based on profiled noise characteristics. Additionally, the ambient sleep system 100 may learn and adjust noise characteristics to identify states of a user.

Figure 1B:
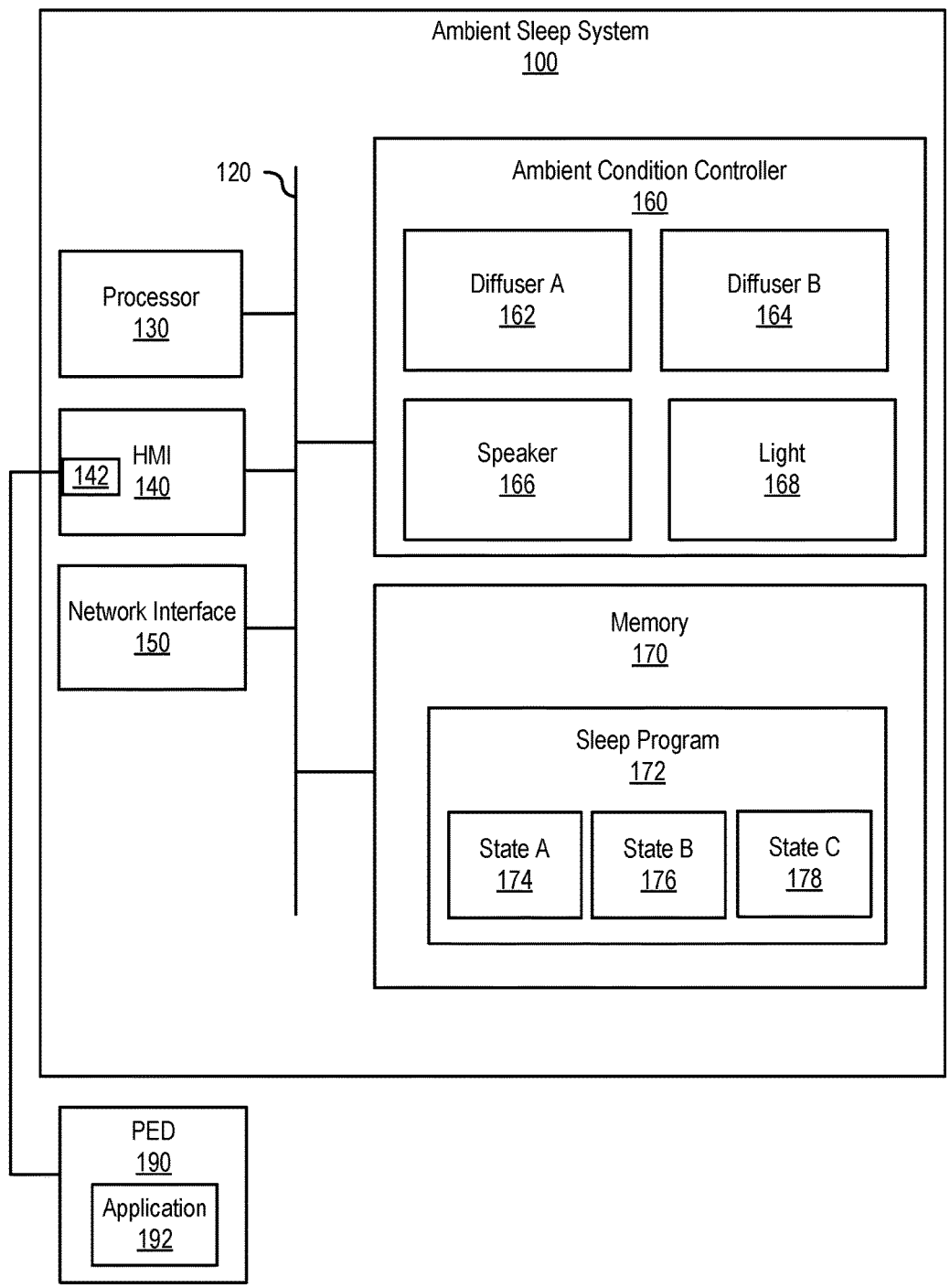
FIG. 1B is a block diagram of an ambient sleep system coupled to a personal electronic device, according to one embodiment.

FIG. 1B is a block diagram of an ambient sleep system 100 coupled to a personal electronic device 190, according to one embodiment. As shown, in addition to the features described with reference to FIG. 1A, the ambient sleep system may include some type of network interface 150 and couple with a PED 190 through a physical connection 142. The physical connection 142 may be a USB port, lightening port, or other powered data port.

The ambient sleep system 100 may communicate with, control, and charge the connected PED 190 through the physical connection 142. For example, the ambient sleep system 100 may suppress the PED's notifications. Additionally, the ambient sleep system 100 may use the features of the PED 190 to generate an ambient condition. For example, the ambient sleep system 100 may use the screen of the PED 190 as a light. The ambient sleep system 100 may also use the speaker of the PED 190 to generate sound for the ambient condition.

The PED 190 may have an application 192 installed thereon that enables the PED 190 to communicate with and control the ambient sleep system 100. The application 192 may provide a graphical user interface to adjust settings on the ambient sleep system. The application 192 may also allow a user to create ambient programs such as the sleep program discussed with reference to FIG. 2. The PED 190 may also communicate with the ambient sleep system over the network interface 150.

The network interface 394 may facilitate communication with other computing devices, networks and/or remote devices including the PED 190. The network interface 394 may be equipped with conventional network connectivity, such as, for example, Bluetooth, Ethernet (IEEE 802.3), Token Ring (IEEE 802.5), Fiber Distributed Datalink Interface (FDDI), or Asynchronous Transfer Mode (ATM). The network interface 150 may be one or more wireless transceivers, such as, for example, a WI-FI transceiver, Bluetooth transceiver, ZigBee transceiver, or the like. Further, the network interface 394 may be configured to support a variety of network protocols such as, for example, Internet Protocol (IP), Transfer Control Protocol (TCP), Network File System over UDP/TCP, Server Message Block (SMB), MICROSOFT® Common Internet File System (CIFS), Hypertext Transfer Protocols (HTTP), Direct Access File System (DAFS), File Transfer Protocol (FTP), Real-Time Publish Subscribe (RTPS), Open Systems Interconnection (OSI) protocols, Simple Mail Transfer Protocol (SMTP), Secure Shell (SSH), Secure Socket Layer (SSL), and so forth.

The network interface 150 may be used to communicate with remote devices that can enhance the ambient conditions. For example, the network interface 150 may connect the ambient sleep system 100 to a home automation system, a thermostat, a home lighting system, or the like. The sleep program 172 may provide operating parameters for remote devices as well as the ambient condition controller. In some embodiments, the network interface 150 may communicate with other ambient sleep systems. In such embodiments, the sleep programs, states, and other configuration of one ambient sleep system may be transmitted to another sleep system.

Figure 1C:
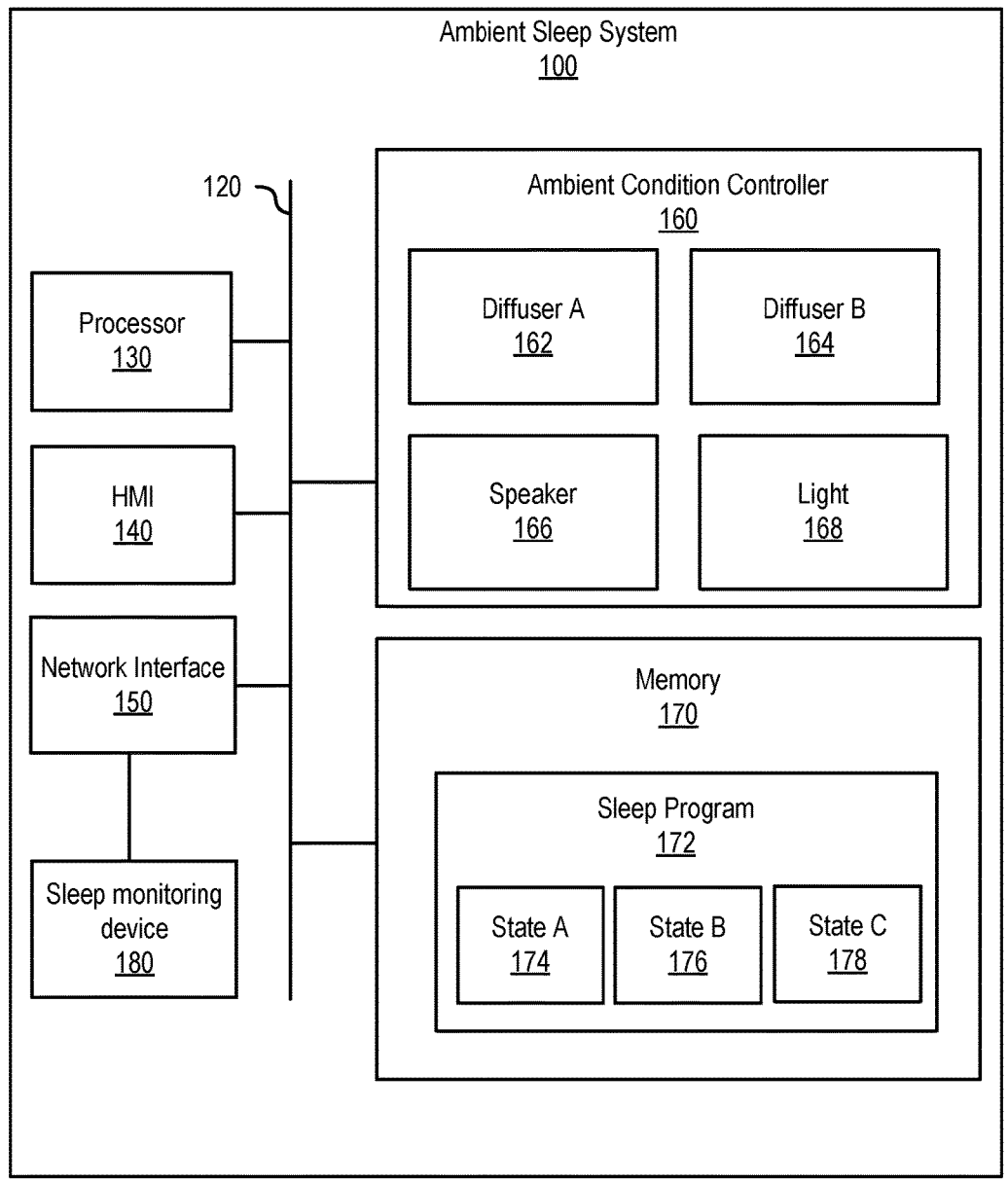
FIG. 1C is a block diagram of an ambient sleep system with a sleep monitoring device, according to one embodiment.

FIG. 1C is a block diagram of an ambient sleep system 100 with a sleep monitoring device 180, according to one embodiment As shown, in addition to the features described with reference to FIGS. 1A and 1B, the ambient sleep system may include a sleep monitoring device 180. In other embodiments, the sleep monitoring device may be an external third party device. The sleep monitoring device 180 may capture information regarding the user's state (awake, asleep, sleep cycle, etc.). Based on the state of the user, the ambient sleep monitor may configure the ambient condition controller to a corresponding state. For example, if the sleep monitoring device detects that the user is falling to sleep, the ambient condition controller 160 may be configured in state A 174. Additionally, the length of each ambient condition controller state 174, 176, 178 may be determined based on the sleep monitoring data from the sleep monitoring device 180.

Figure 2:
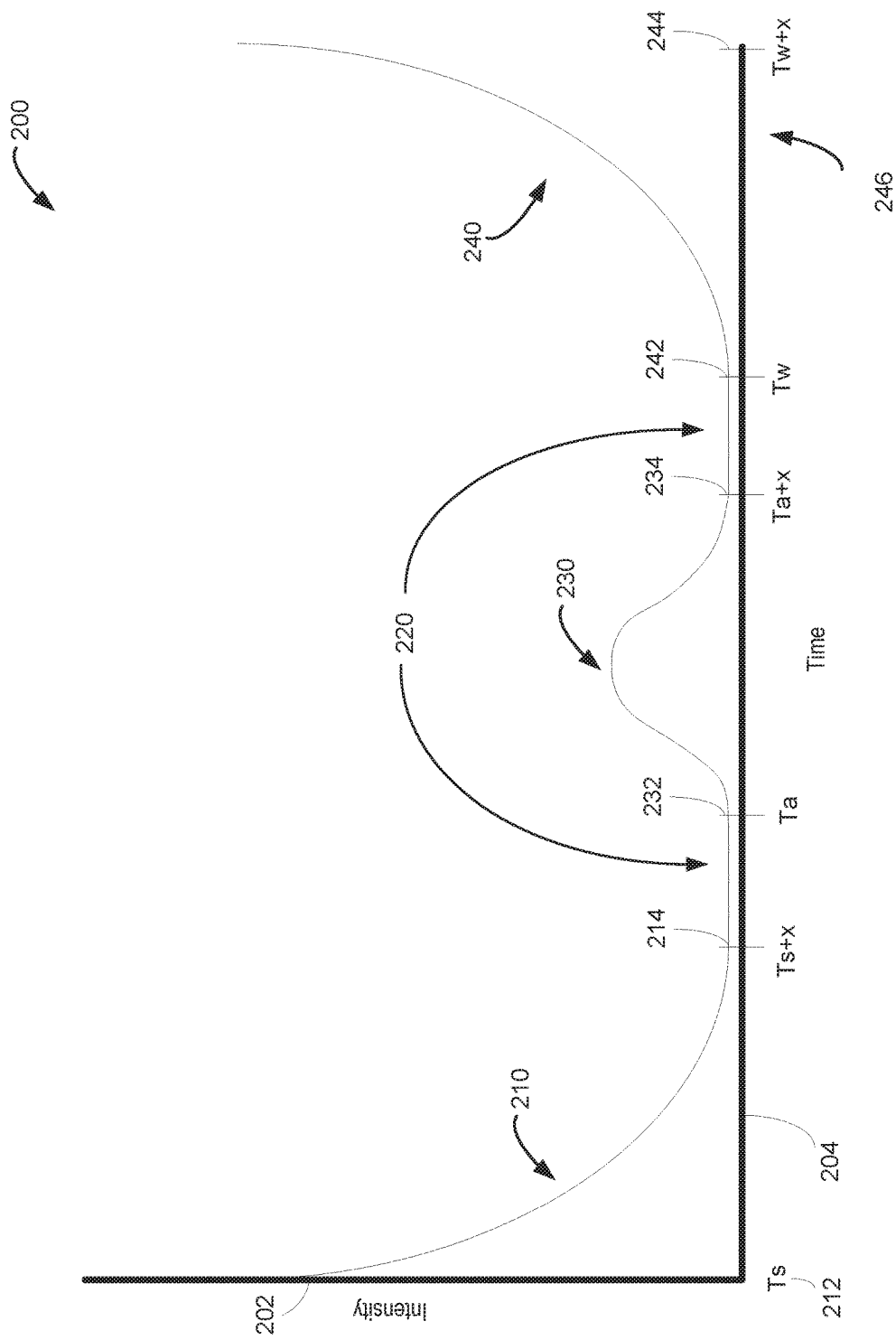
FIG. 2 is a graph depicting a sleep program, according to one embodiment.

FIG. 2 is a graph depicting a sleep program 200, according to one embodiment. The sleep program 200 is illustrated as an ambient condition intensity 202 along a timeline 204. The ambient condition measured may include sound, light, and/or scent. Accordingly, the ambient condition intensity 202 may be measured in decibels, lumens, hues, or concentration. The illustrated sleep program 200 may be configured by the user. The sleep program 200 may be comprised of four phases: a relax phase 210, a sleep phase 220, a soothe phase 230, and a wake phase 240.

The relax phase 210 may be associated with a user falling to sleep. The relax phase 210 may last for a certain duration beginning at time Ts 212 and ending at time Ts+x 214. The duration may be a pre-set constant or adjustable. For example, sleep data from a sleep monitoring device may indicate that the user has fallen to sleep before time Ts+x 214. Instead of continuing to time Ts+x 214, the relax phase 210 may be completed. The relax phase 210 may begin with high intensity ambient conditions and then gradually decrease until Ts+x 214. For example, a light may initially be set to its brightest level, and a diffuser disperse a significant amount of scent. As time Ts+x 214 approaches, the brightness level and scent concentration may be decreased. The gradual decrease of ambient conditions may assist a user in falling to sleep. In some embodiments, the relax phase 210 may simulate a sunset. In other embodiments, the user may select settings that they have found help them relax.

The sleep phase 220 may be associated with a user being asleep. The sleep phase 220 may last for a certain duration beginning at time Ts+x 214 and ending at time Tw 242. The duration may be constant or adjustable. For example, the user may select a desired duration of sleep, a desired number of sleep cycles, or a specific wake time. In some embodiments, the sleep phase 220 may comprise a consistent of low intensity ambient conditions. In some embodiments, the sleep phase 220 may include white noise at a low decibel level and/or scent at a low concentration. In other embodiments, the sleep phase 220 the ambient sleep system may produce no ambient conditions. In yet other embodiments, the ambient sleep system may produce varying ambient conditions based on the sleep stage a user is in. The ambient conditions generated during the sleep phase 220 may assist a user in staying asleep. In some embodiments, the sleep phase 220 may be predefined. In other embodiments, the user may select settings that they have found help them sleep. In yet other embodiments, the same ambient conditions present in the relax phase 210 may be used at a lower intensity.

The sleep phase 220 may be interrupted by the soothe phase 230 if the ambient sleep system detects the user is waking prior to a wake window 246 (i.e., between time Tw 242 and Tw+x 244). The soothe phase 230 may last for a duration beginning at time Ta 232 and ending at time Ta+x 234. The duration may be a pre-set constant or adjustable. For example, sleep data from a sleep monitoring device may indicate that the user has woken up at time Ta 232 and fallen bake to sleep before time Ta+x 234. Instead of continuing to time Ta+x 234, the soothe phase 230 may be completed. The soothe phase 230 may gradually increase in intensity until the ambient conditions reach a target level and then plateau before gradually descending. The ambient conditions generated during the soothe phase 230 may assist a user in falling back to sleep.

In some embodiments, the soothe phase 230 may be predefined. In other embodiments, the user may select settings that they have found help them sleep. In yet other embodiments, the same ambient conditions present in the relax phase 210 or the sleep phase 220 may be used. In some embodiments, the soothe phase 230 may have different ambient conditions based on the alertness of the user. For example, a user rolling over may increase the amount of scent released by the diffuser, whereas a user getting out of bed may turn the light on.

The wake phase 240 may be associated with a user waking up. The wake phase 240 may last for a certain duration beginning at time Tw 242 and ending at time Tw+x 244. The duration may be a pre-set constant or adjustable. For example, the user may set a wake window 246 and a target wake time. The wake window 246 specifying the earliest and latest a user desires to wake up. The wake time may specify the exact time a user desires to wake. The wake time may be the end of the wake window or somewhere in the middle. Further, in some embodiments, the wake phase 240 may begin after the wake window has begun if the sleep ambient system is configured to wait for a user to come out of a sleep cycle. The wake phase 240 may begin with low intensity ambient conditions and then gradually increase until time Tw+x 244. After time Tw+x 244, the ambient sleep system may maintain ambient conditions for a set period of time or until a user indicates he is awake. The gradual increase of ambient conditions may assist a user in waking up. In some embodiments, the relax phase 210 may simulate a sunrise. In other embodiments, the user may select settings that they have found help them wake up.

The settings for each phase may be changed prior to the beginning of the phase or during the phase. The changes may be persistent or only last for one program cycle. In some embodiments, the changes made to a phase may be averaged overtime. For example, if the user is falling to sleep at different times, the ambient sleep system may average the different times. In yet other embodiments, the ambient sleep system may detect sleep patterns and adjust the phases accordingly. The user may select certain settings/ambient conditions as favorites. The ambient sleep monitor may make suggestions on future sleep programs based on favorites and past history. The scents, sounds, and lighting associated with each phase may be different from each other. The changes may be mad via an application on a smart phone, or inputs on the ambient sleep system.

Figure 3:
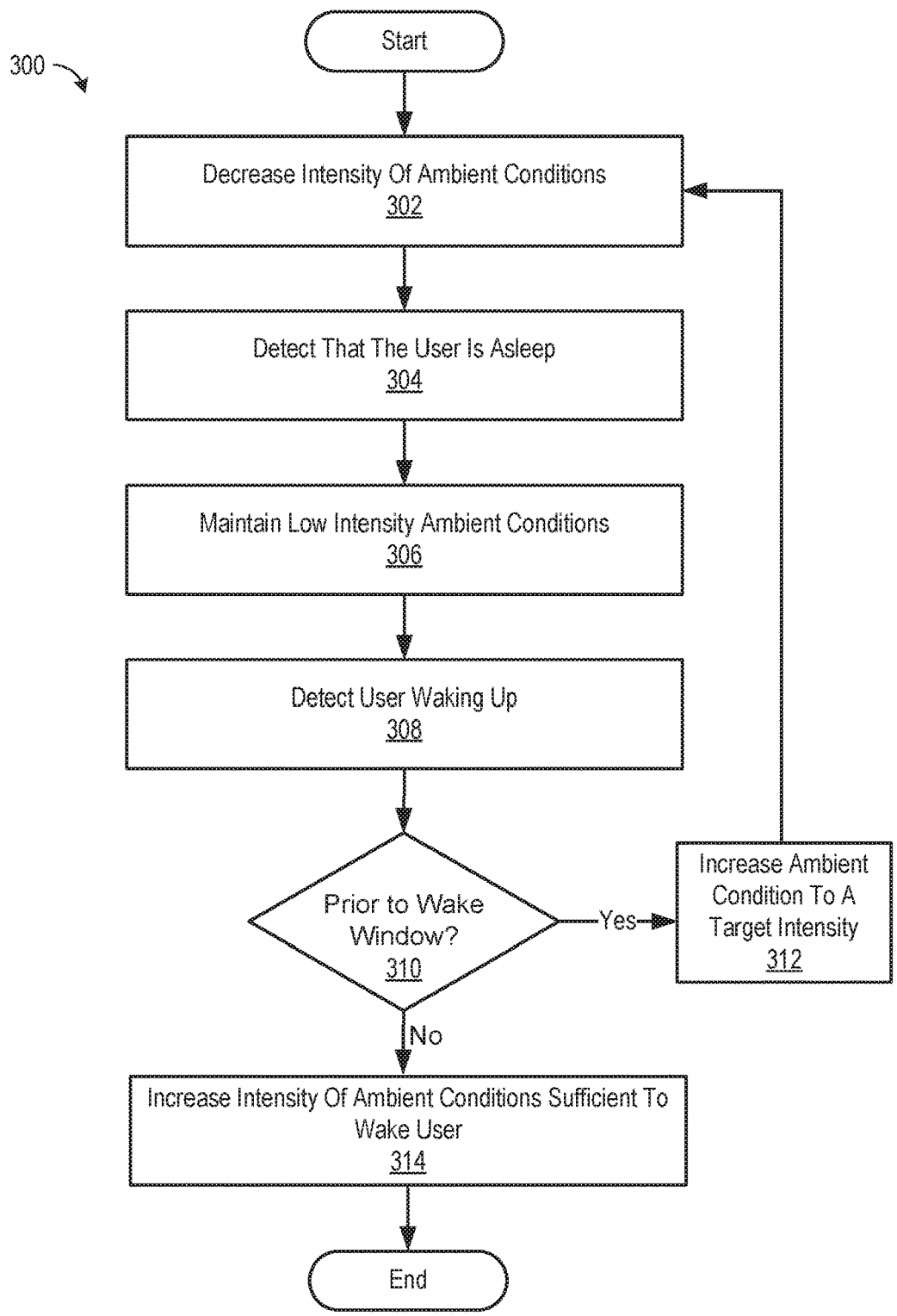
FIG. 3 is a flow chart of one embodiment of a method for generating ambient sleep conditions based on sleep monitoring data.

FIG. 3 is a flow chart of one embodiment of a method 300 for generating ambient sleep conditions based on sleep monitoring data. The steps of FIG. 3 may be implemented by the ambient sleep system (e.g., ambient sleep system 100). The ambient sleep system may be configured to implement the method 300 by use of one or more instructions stored on a machine-readable storage medium. The storage medium may be non-transitory, such as a hard disk, solid-state memory, electrically erasable memory, or the like.

An ambient condition controller may decrease 302 the intensity of ambient conditions. The decrease 302 may be gradual so as to encourage a user to relax and/or fall to sleep. A sleep monitoring device may detect 304 that the user is asleep. Based on that detection, the ambient condition controller may maintain 306 low intensity ambient conditions, such as a faint scent.

The sleep monitoring device may further detect 308 if the user is waking up. The ambient sleep system may compare a current time to a preconfigured wake window 310. If the current time is prior 310 to the wake window, the ambient condition controller may increase 312 ambient conditions to a target intensity. The target intensity may be a fraction of an original intensity prior to decreasing 302 the intensity of the ambient conditions. In some embodiments, the target intensity may be the intensity at the moment the user was detected 304 asleep. This slight increase of intensity may assist the user in falling back to sleep. If the current time is not prior 310 to the wake window, the ambient condition controller may increase 314 the intensity of the ambient conditions sufficient to wake the user.

Figure 4:
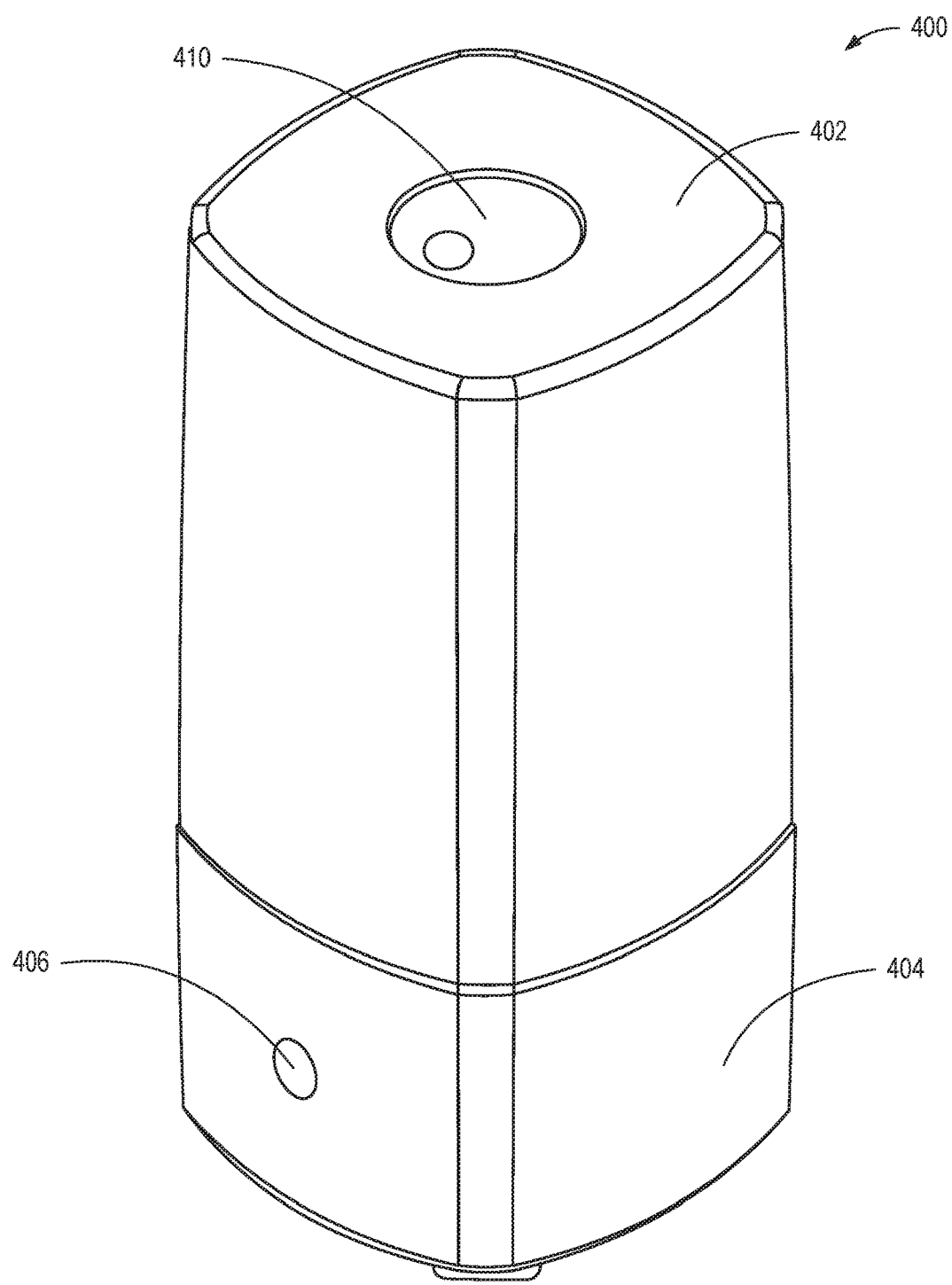
FIG. 4 is a perspective view of an ambient sleep system, according to one embodiment.

FIG. 4 is a perspective view of an ambient sleep system 400. In the illustrated embodiment, the ambient sleep system 400 includes a base 404 and a shade 402. The ambient sleep system 400 embodiment shown is sized and shaped to function as a lamp on an end table. In other embodiments, the ambient sleep system may be designed as a floor lamp.

The base 404 may include controls to configure the ambient sleep system 400 based on user input. As shown, the controls may include a button 406. The button 406 may be mechanical or capacitive and be configured to receive a user input.

While the ambient sleep system 400 has only one control in the embodiment shown, the button 406 may be able to receive a plurality of user inputs. The user input may include but is not limited to a touch, swipe, or hold. Each user input may control different aspects of the ambient sleep system 400. For example, touching the button 406 may cause the lights of the ambient sleep system 400 to turn on. Whereas, swiping across the button 406 in an upward direction may increase the audio volume of the ambient sleep system.

The ambient sleep system 400 action (e.g., adjust lighting, scent, or sound) associated with a user input may vary based on a variety of factors. In some embodiments, the user inputs trigger different actions based on the time the user input was received. For example, pressing the button 406 at night may begin a sleep program, and pressing the button 406 in the morning may begin a wake program. In some embodiments, environmental factors, may alter the action associated with a user input. For example, the ambient sleep system 400 may include a light sensor that detects the presence and intensity of exterior light. Based on the intensity of exterior light, the ambient sleep system 400 may adjust its initial light output when a user input associated with turning on the light is received. In some embodiments, the user inputs trigger different actions based on the current state of the ambient sleep system 400. For instance, a user input received during a sleep program may cause a different action than a user input received after a wake program.

The shade 402 may be semi-opaque and configured to diffuse light. In some embodiments, the shade 402 is configured to be more translucent to certain light wavelengths. In such embodiments, the brightness of the ambient sleep system depends on the intensity and frequency of the system lights. In some embodiments, a plurality of shades with varying opacities are interchangeable to alter the lighting of the ambient sleep system 400.

In the illustrated embodiment, the shade 402 includes an opening for scents to pass. In some embodiments, a shade may be permeable, thereby allowing the scent to be released without an opening. The opening may house a director 410. The director 410 may alter the amount of each scent and/or the direction at which the scent is released.

Figure 5:
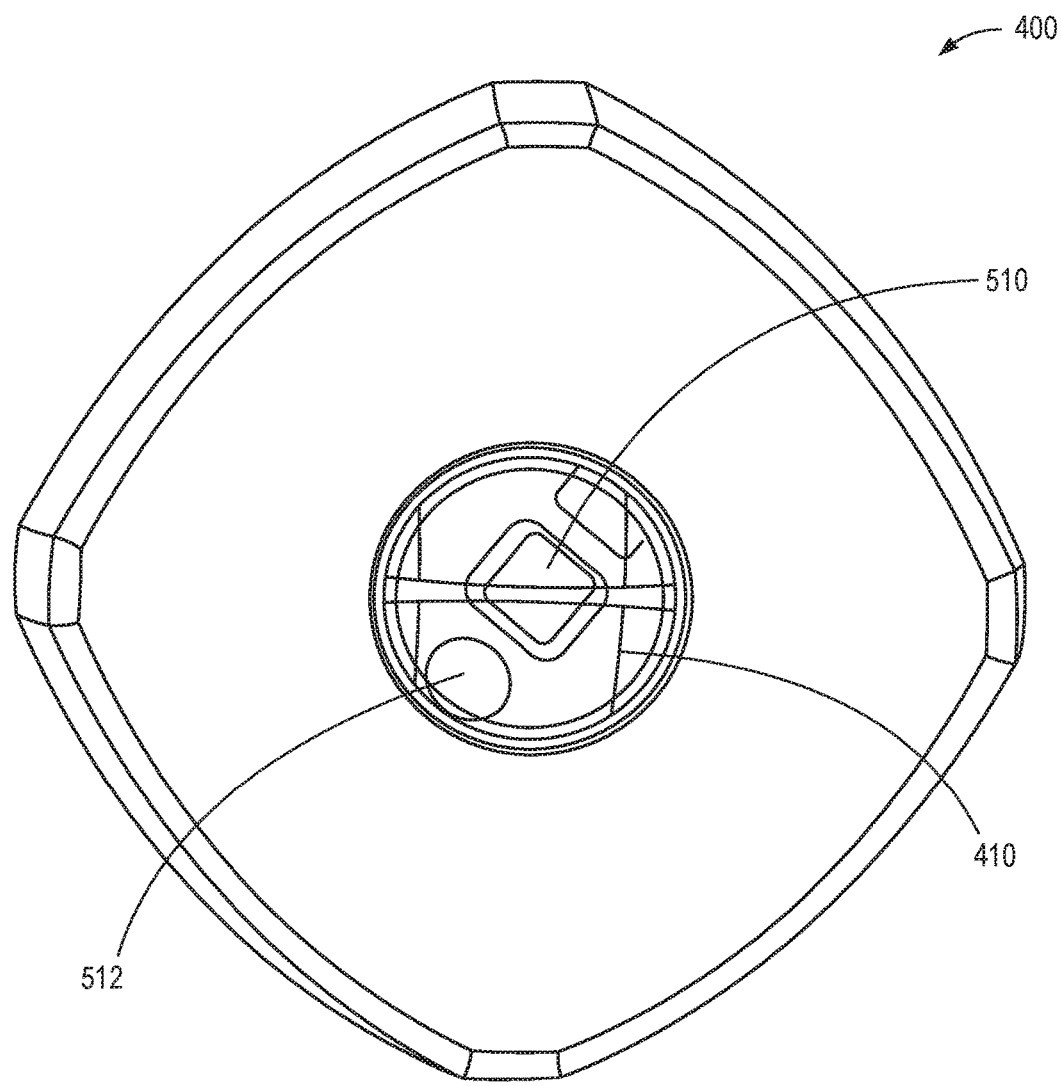
FIG. 5 is a top view of an ambient sleep system, according to one embodiment.

FIG. 5 is a top view of an ambient sleep system 400. The director 410 may direct scents as they are released from the ambient sleep system 400. As shown, the director 410 may include a vent 510 and a notch 512. The vent 400 is angled relative to the top of the ambient sleep system 400 to direct any escaping scents in a lateral direction. In some embodiments, the angle may be selectively adjusted by the user or the ambient sleep system 400. The notch 512 may assist a user in adjusting the direction of the vent 400. For instance, a user may insert a finger in the notch and rotate the director. In some embodiments, rotating the director may alter how multiple scents are blended.

Figure 6:
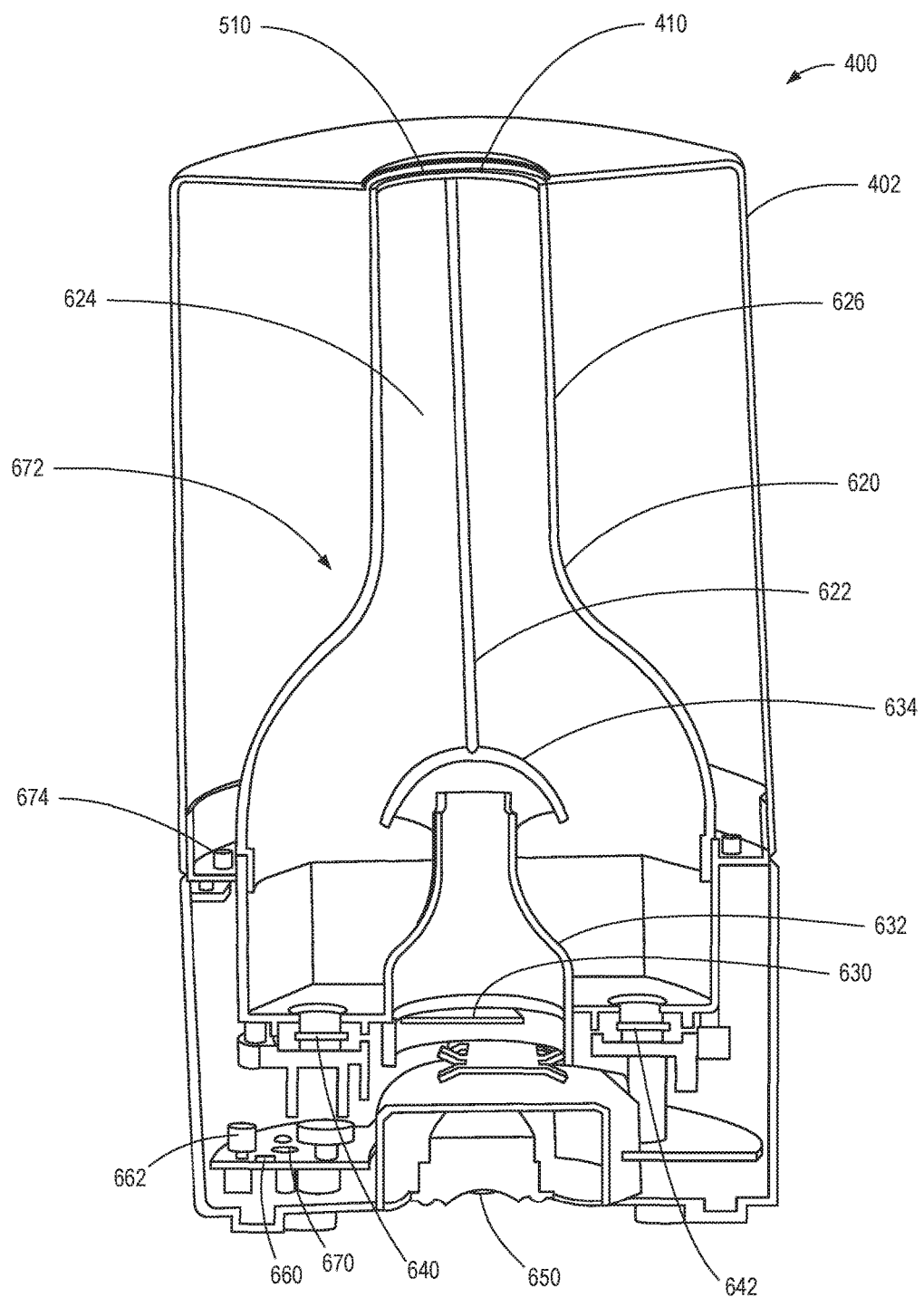
FIG. 6 is a cutaway view of an ambient sleep system, according to one embodiment.

FIG. 6 is a cutaway view of an ambient sleep system 400, according to one embodiment. The ambient sleep system 400 may include a processor 660, ambient condition controller 670, and a storage medium 662. The storage medium has instructions that, when executed by the processor 660, cause the processor 660 to implement an ambience program. During the ambience program, the ambient condition controller 670 may adjust the lighting, the sound, and/or the scent produced by the ambient sleep system 400.

The ambience program may be stored by the storage medium. In some embodiments, the ambience program may be stored by another device such as a smartphone. The ambient sleep system 400 may receive an ambience program stored on an external device through a physical connection, such as a USB, or wirelessly. In some embodiments, the ambience program may adjust based on what external device is in communication with the ambient sleep system 400.

The ambient condition controller 670 controls the illumination device 674, diffusing system 672, and speaker 650 of the ambient sleep system 400 to generate an ambient condition. For example, the ambient condition controller system 400 may receive a desired ambient condition from a user, and the ambient condition controller 670 may alter the state of the ambient sleep system 400 to generate a corresponding visual, auditory, and olfactory scene. In some embodiments, the ambient condition controller 670 may be configured to control external systems.

The illumination device 674 may include internal lighting as shown. In some embodiments, the lighting may include light-emitting diodes. The illumination device 674 may adjust the lighting intensity, frequency, and color. In some embodiments, the ambient condition controller 670 may also control external room lighting.

In some embodiments, the illumination device 674 provides directional light to assist a user. For example, the illumination device 674 may provide directional lighting suitable for reading. This may allow a person to read a book in the same room that another person is sleeping. In some embodiments, the illumination device 674 may provide directional lighting to assist a user in walking around a room at night. For instance, the ambient sleep system 400 may detect a user getting out of bed, and turn on a light that illuminates a path towards a door. The direction of the light path may be preset by the user, or a motion detector may guide the direction of the light path. Providing a light path may provide visual assistance to the user without the need to illuminate the entire room. By not illuminating the entire room, other occupants of the room may not be disturbed and the user may have an easier time going back to sleep when returning to bed.

The directional lighting may operate concurrently with an ambience programs to avoid interruption to the program. Alternatively, activation of the directional lighting may pause an ambience program. For example, in some embodiments, getting out of bed pauses a sleep program, and returning to bed resumes the sleep program. In some embodiments, an sleep program continues to run while a directional reading light is in operation.

The diffusing system 672 includes a plurality of diffusers (e.g., diffuser 640 and 642). The diffusers 640, 642 may be configured to diffuse different scents. The scents may be dispersed individually or in some combination. In some embodiments, the diffusers 640, 642 may be ultrasonic diffusers that break oil particles to micro-molecules to diffuse the oil into the air as ions. The diffusing system 672 may control the rate at which each diffuser breaks apart particles.

The diffusing system 672 includes a fan 630 to assist scent dispersal. The speed of the fan 630 may be adjusted to alter the flow of scents. As shown, a funnel 632 and a nozzle 634 direct the air flow from the fan 630. The nozzle 634 is configured to guide the airflow towards the diffusers 640, 642. The nozzle 634 may provide control over the released combination scents. For example, in some embodiments, the diffusing system 672 may pivot the nozzle 634 to increase airflow to a first diffuser and decrease airflow to a second diffuser. The fan 630 may also cool the processor 660. The ambient condition controller 670 may also use the fan 630 as a white noise.

The ions diffused by the diffusers 640, 642 exit the ambient sleep system 400 through an exit funnel 620. The exit funnel 620 is split into two chamber 624, 626 by a divider 622. As shown, in some embodiments, the divider 622 may separate the ions until reaching the director 410. This may limit cross-contamination between the oils. The director 410 may direct and mix the ions as they exit the vent 510.

Figure 7:
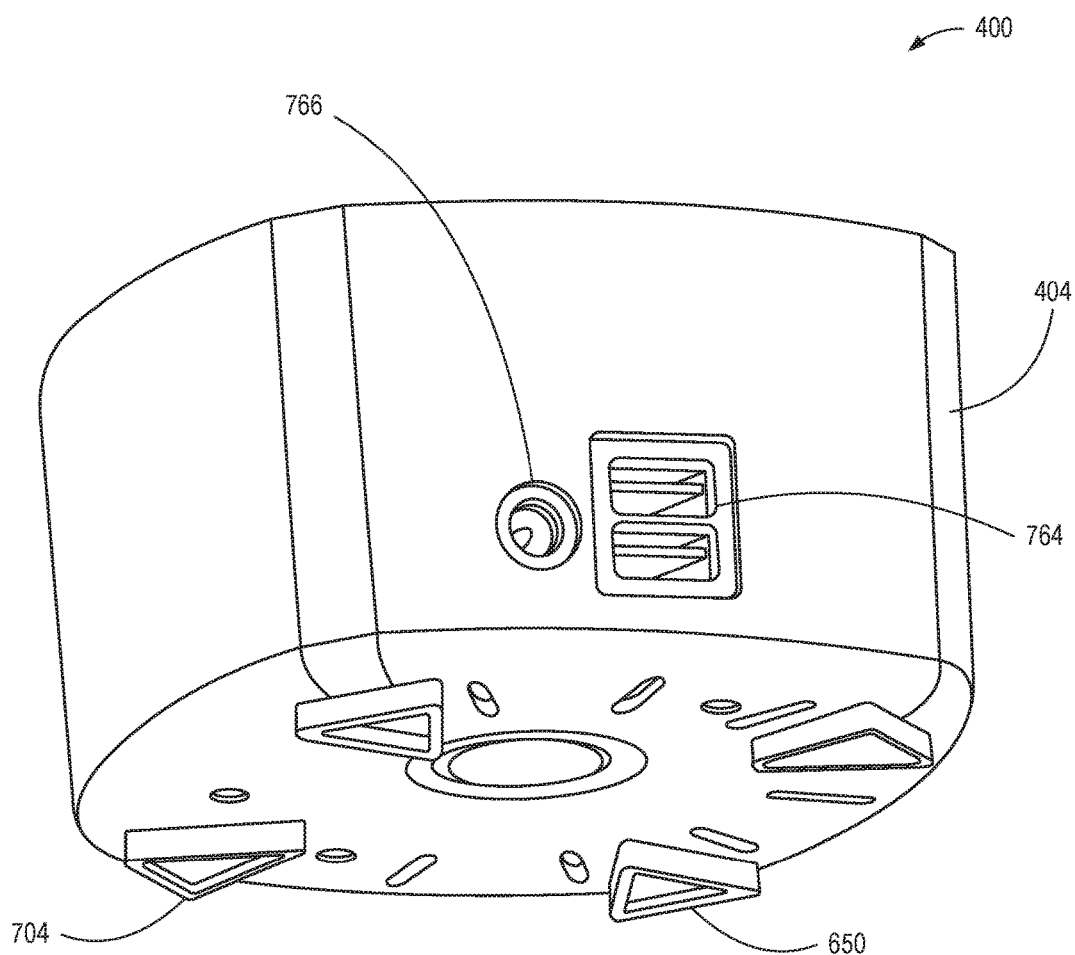
FIG. 7 is a base of an ambient sleep system, according to one embodiment.

FIG. 7 is a base 404 of an ambient sleep system 400, according to one embodiments. The base 404 may be removed from the upper elements of the ambient sleep system (e.g., shade 402 and exit funnel 620 in FIG. 6). This provides access to the diffusers to allow a user to refill the diffusers. As shown, in some embodiments, the speaker 650 may be configured to project sound out of the bottom of the ambient sleep system 400. The feet 704 of the base 404 may hold the base 404 above a surface prevent muffled sound from the speaker 650. The base 404 also includes a plurality of interfaces.

As shown, in some embodiments, the base 404 may include multiple USB ports 764 and an audio output 766. The USB ports 764 may provide power to personal electronic devices. USB connection to pair with personal electronic devices. In some embodiments, ambient sleep system 400 may require a physical connection through the USB ports 764 with a personal electronic device for an initial pairing to increase security. The ambient sleep system 400 may control settings on the personal electronic device through the USB ports 764.

Figure 8:
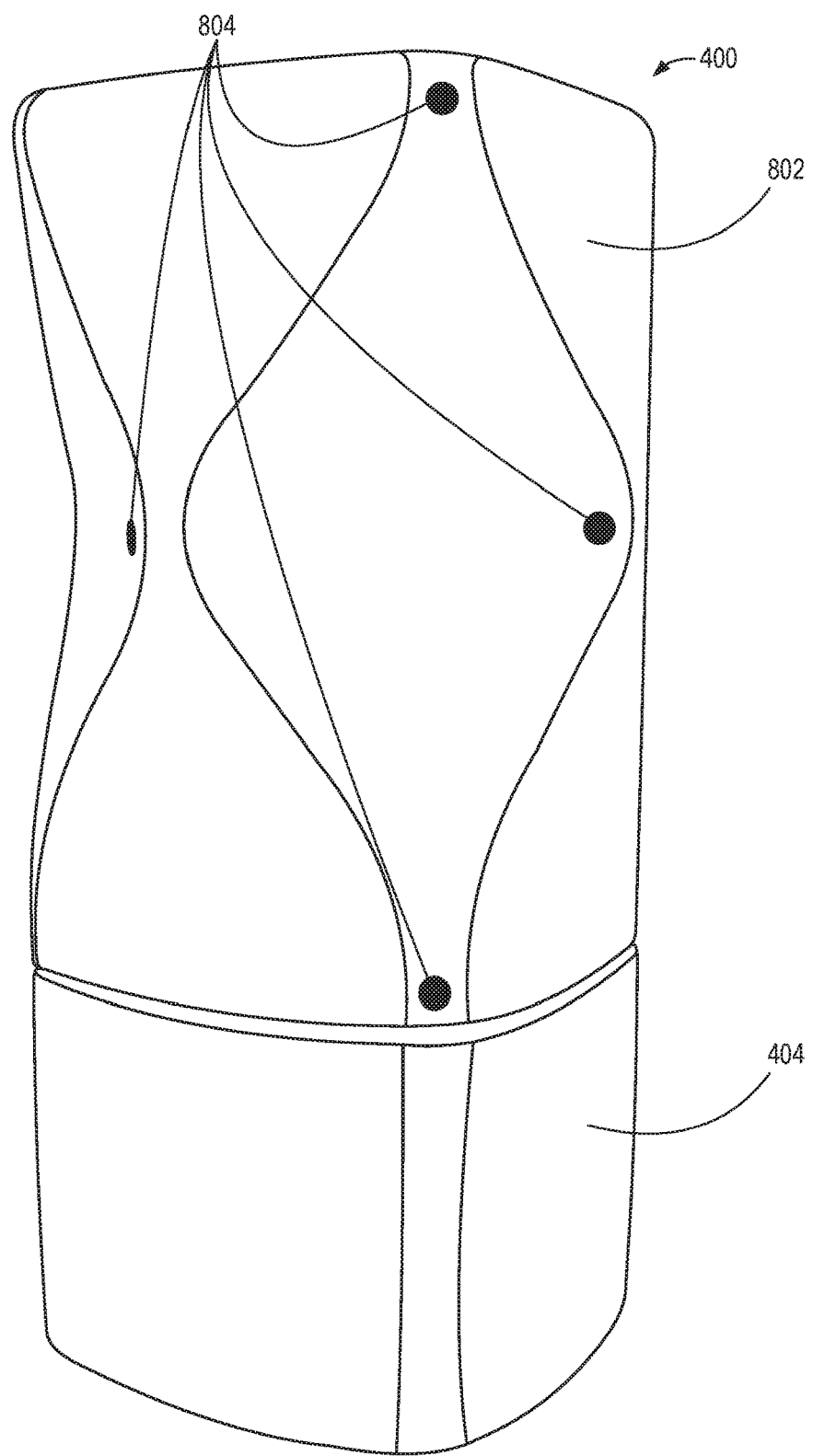
FIG. 8 is an ambient sleep system with a replacement shade, according to one embodiment.

FIG. 8 is an ambient sleep system 400 with a replacement shade 802, according to one embodiment. As shown, the shad 402 in FIG. 4 has been replaced with replacement shade 802. As shown, in some embodiments, the replacement shade 802 provides an alternative aesthetic design.

In some embodiments, the replacement shade 802 provides additional functionalities. For example, apertures 804 may selectively provide directional lighting. For example, in some embodiments, the apertures may be placed at varying angles and be configured to open and close to direct light in a specific direction. The light may be from the base 404. In some embodiments, the shade 802 may include a plurality of light emitting diodes. The replacement shade's 802 light emitting diodes may have a different range of temperatures, colors, and flicker rates than the lights in the base 404. The coupling between the base 404 and the replacement shade 802 may provide an electrical connection for power and communication. Additional functionalities of replacement shades may include directing, modifying, or amplify sounds and scents.

Coupling the replacement shade 802 to the base 404 may automatically update or load ambience programs. The updated or new ambience programs may be based on the characteristics and functionalities of the replacement shade 802. In some embodiments, ambience programs associated with replacements shades are preloaded on the ambient sleep system 400, and coupling one of the replacement shades unlocks ambience programs corresponding to that replacement shade. The coupling may be physical or electrical connections. For example, in some embodiments the replacement shade 802 may change the positions of a plurality of switches on the base 404. In some embodiments, an NFC tag on the replacement shade 802 may be read by an NFC reader on the base 404.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of one or more of the terms "about," "approximately," "substantially," and "generally." For each such reference, it is to be understood that, in some embodiments, the value, feature, or characteristic may be specified without approximation. For example, where such a qualifier is used, the term includes within its scope the qualified word in the absence of the qualifier.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment. Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any embodiment requires every feature shown in a particular drawing.

Unless otherwise noted, the terms "a" or "an" are to be construed as meaning "at least one of." In addition, for ease of use, the words "including" and "having" are interchangeable with and have the same meaning as the word "comprising." Recitation of the term "first" with respect to a feature or element does not necessarily imply the existence of a second or additional such feature or element.

We claim:

1. A system for generating ambient conditions to improve sleep, comprising:
   a processor;
   an ambient condition controller comprising:
      an exit funnel,
      a first diffuser configured to diffuse a first scent through a first chamber of the exit funnel,
      a second diffuser, separate from the first diffuser, the second diffuser configured to diffuse a second scent through a second chamber of the exit funnel, and
      a divider separating the first chamber from the second chamber; and
   a computer-readable non-transitory storage medium having instructions that, when executed by the processor, are configured to cause the processor to implement a sleep program, comprising:
      configuring the ambient condition controller to enter a first state corresponding to a user falling to sleep, wherein entering the first state comprises the ambient condition controller configuring the first diffuser to diffuse the first scent, and
      configuring the ambient condition controller to enter a second state corresponding to the user waking up within a target time period, wherein entering the second state comprises the ambient condition controller configuring the second diffuser to diffuse the second scent.

2. The system of claim 1, wherein the processor is configured to receive sleep monitoring data pertaining to the user.

3. The system of claim 2, wherein implementing the sleep program further comprises:
   configuring the ambient condition controller to enter a third state corresponding to the user being asleep based on the received sleep monitoring data.

4. The system of claim 2, wherein implementing the sleep program further comprises:
   increasing the first scent being diffused by the first diffuser in response to the received sleep monitoring data indicating that the user is waking up prior to the target time period.

5. The system of claim 1, wherein:
   the ambient condition controller further comprises a speaker,
   configuring the ambient condition controller to enter the first state comprises configuring the speaker to emit first sounds, and
   configuring the ambient condition controller to enter the second state comprises configuring the speaker to emit second sounds, different from the first sounds.

6. The system of claim 1, further comprising an interface configured to receive a first user input indicating that the user desires to reduce a length of time spent in the first state while the ambient condition controller is in the first state.

7. The system of claim 1, further comprising a clock, wherein the ambient condition controller is configured to enter one or more of the first state and the second state at a specified time indicated by the clock.

8. The system of claim 1, wherein the one or more of the first state and the second state are user configurable.

9. The system of claim 1, wherein implementing the sleep program further comprises:

configuring the first diffuser to disperse a first quantity of the first scent in response to entering the first state, and decreasing the quantity of the first scent dispersed by the first diffuser while the ambient condition controller remains in the first state.

10. The system of claim 1, wherein implementing the sleep program further comprises:

configuring the second diffuser to disperse a first quantity of the second scent in response to entering the second state, and increasing the quantity of the second scent dispersed by the second diffuser while the ambient condition controller remains in the second state.

11. An apparatus for generating ambient conditions to improve sleep, comprising:
a processor;
an ambient condition controller in communication with the processor, comprising:
an exit funnel;
a first diffuser configured to diffuse a first scent through a first portion of the exit funnel,
a second diffuser configured to diffuse a second scent through a second portion of the exit funnel, and
a divider configured to isolate the first portion of the exit funnel from the second portion of the exit funnel; and
a computer-readable non-transitory storage medium having instructions that, when executed by the processor, are configured to cause the processor to implement a sleep program, comprising configuring the ambient condition controller to:
enter a first state configured to assist a user in falling asleep, wherein entering the first state comprises configuring the ambient condition controller to use the first diffuser to diffuse the first scent and to prevent the second diffuser from diffusing the second scent, and
enter a second state configured to assist the user in awakening from sleep, wherein entering the second state comprises configuring the ambient condition controller to use the second diffuser to diffuse the second scent and to prevent the first diffuser from diffusing the first scent.

12. The apparatus of claim 11, wherein implementing the sleep program further comprises configuring the ambient condition controller to:
disperse a first concentration of the first scent in response to entering the first state;
gradually decrease dispersal of the first scent towards a second concentration while in the first state; and
enter a third state configured to assist the user in returning to sleep, wherein entering the third state comprises configuring the ambient condition controller to disperse a third concentration of the first scent in response to entering the third state, the third concentration lower than the first concentration and higher than the second concentrations.

13. The apparatus of claim 11, wherein the ambient condition controller further comprises a nozzle configured to selectively guide airflow to one of the first diffuser and the second diffuser.

14. The apparatus of claim 13, wherein entering the first state further comprises the ambient condition controller configuring the nozzle to selectively guide the airflow to the first diffuser.

15. The apparatus of claim 13, wherein entering the second state further comprises the ambient condition controller configuring the nozzle to selectively guide the airflow to the second diffuser.

16. The apparatus of claim 11, wherein:
the ambient condition controller further comprises an illumination device; and
implementing the sleep program further comprises configuring the ambient condition controller to:
configure the illumination device to operate at a first brightness level in response to entering the first state, and
gradually decrease the brightness level of the illumination device towards a second brightness level while in the first state.

17. The apparatus of claim 11, wherein:
the ambient condition controller further comprises an illumination device; and
implementing the sleep program further comprises configuring the ambient condition controller to:
configure the illumination device to operate at a first brightness level in response to entering the second state, and
gradually increase the brightness level of the illumination device towards a second brightness level while in the second state.

18. The apparatus of claim 11, wherein implementing the sleep program further comprises configuring the ambient condition controller to remain in the first state until one or more of:
reaching a specified end time for the first state; and
receiving sleep monitoring data indicating that the user is asleep.

19. The apparatus of claim 18, wherein implementing the sleep program further comprises configuring the ambient condition controller to:
gradually decrease a concentration of the first scent diffused by the first diffuser while in the first state from a first concentration towards a second concentration, lower than the first concentration;
enter a third state configured to assist the user in remaining asleep, wherein entering the third state comprises configuring the ambient condition controller to use the first diffuser to diffuse a third concentration of the first scent, the third concentration lower than the second concentration; and
enter a fourth state configured to assist the user in falling back asleep, wherein entering the fourth state comprises configuring the ambient condition controller to use the first diffuser to diffuse a fourth concentration of the first scent, the fourth concentration higher than the second concentration.

20. The system of claim 19, wherein implementing the sleep program further comprises configuring the ambient condition controller to:
enter the second state in response to one or more of:
a clock reaching a specified wake time, and
receiving sleep monitoring data indicating that the user is awakening during the target time period; and
gradually increase a concentration of the second scent diffused by the second diffuser while in the second state.

* * * * *